United States Patent [19]

Gibeault et al.

[11] Patent Number: 5,773,709
[45] Date of Patent: Jun. 30, 1998

[54] METHOD AND APPARATUS FOR THERMALLY INDUCING CIRCULATION OF FLUID BETWEEN THE INTERIOR OF A SYSTEM AND A FLUID POCKET ATTACHED THERETO

[75] Inventors: Jean-Pierre Gibeault, Dollard-des-Ormeaux; Claude Beauchemin, Valleyfield, both of Canada

[73] Assignee: Syprotec Inc., Pointe-Claire, Canada

[21] Appl. No.: 674,006

[22] Filed: Jul. 1, 1996

[30] Foreign Application Priority Data

Jun. 28, 1996 [CA] Canada ................................. 2180233

[51] Int. Cl.⁶ .......................... G01N 25/06; G01N 25/56
[52] U.S. Cl. ........................ 73/25.01; 73/19.1; 73/25.04; 73/25.05; 73/61.46; 73/61.76
[58] Field of Search ................................. 73/25.01, 19.1, 73/19.12, 25.04, 25.05, 61.46, 61.76

[56] References Cited

U.S. PATENT DOCUMENTS

| 4,025,412 | 5/1977 | LaConti . |
| 4,112,737 | 9/1978 | Morgan . |
| 4,170,455 | 10/1979 | Henrie ................................. 73/25.04 X |
| 4,271,474 | 6/1981 | Belanger et al. . |
| 4,293,399 | 10/1981 | Belanger et al. . |
| 4,295,368 | 10/1981 | Jannone ............................... 73/61.76 X |
| 4,324,632 | 4/1982 | Tantram et al. . |
| 4,402,211 | 9/1983 | Sugawara et al. . |
| 4,444,040 | 4/1984 | Sakai et al. . |
| 4,715,236 | 12/1987 | Willert . |
| 4,763,514 | 8/1988 | Naito et al. . |
| 5,070,738 | 12/1991 | Morgan . |
| 5,271,263 | 12/1993 | Gibeault ................................ 73/19.12 |

FOREIGN PATENT DOCUMENTS

| 1082774 | 7/1980 | Canada . |
| 61-056774 | 12/1986 | Japan ...................................... 73/19.1 |
| 2170909 | 8/1986 | United Kingdom .................. 73/61.46 |

Primary Examiner—Hezron E. Williams
Assistant Examiner—Daniel S. Larkin
Attorney, Agent, or Firm—Ronald S. Kosie; Robert Brouillette

[57] ABSTRACT

A method and apparatus for inducing circulation of a fluid in an interior of a system between such interior and a fluid pocket. The fluid pocket is connected to a fluid access opening of the system for fluid communication between the fluid pocket and the interior of the system. The method comprises modulating the temperature of a heat transfer element in thermal communication with fluid in the pocket, between a first temperature and a second temperature. A representative fluid sample may be taken from the fluid pocket for analysis.

42 Claims, 11 Drawing Sheets

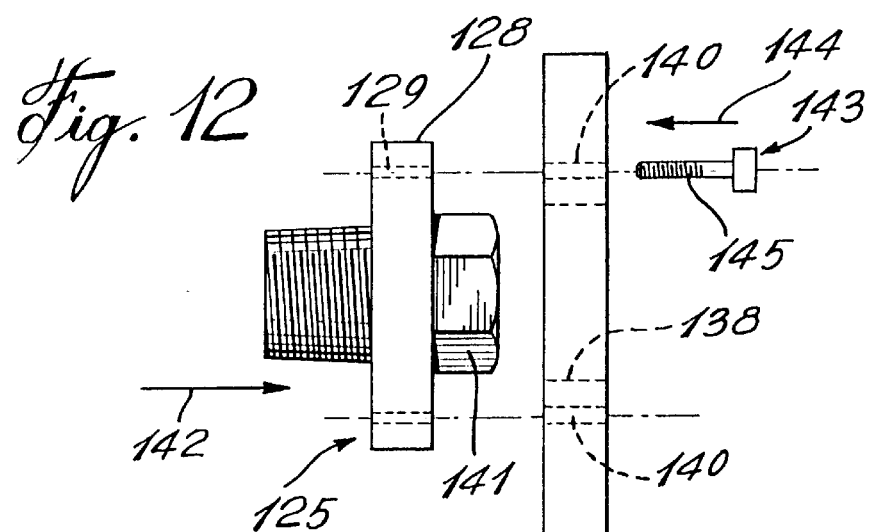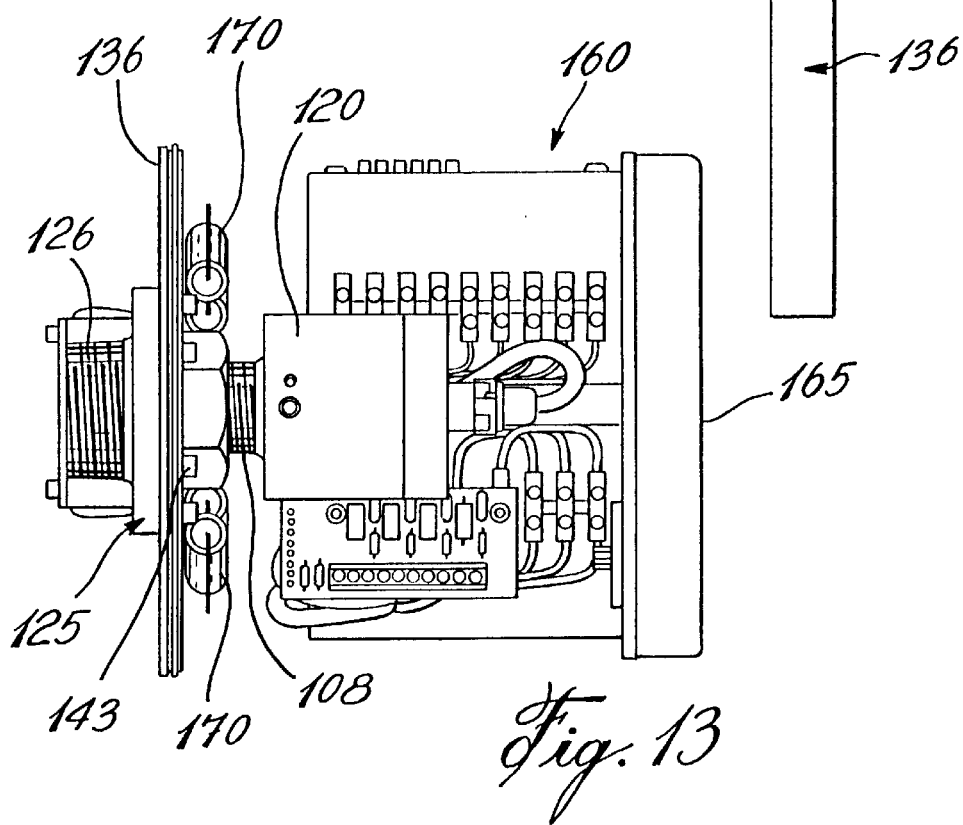

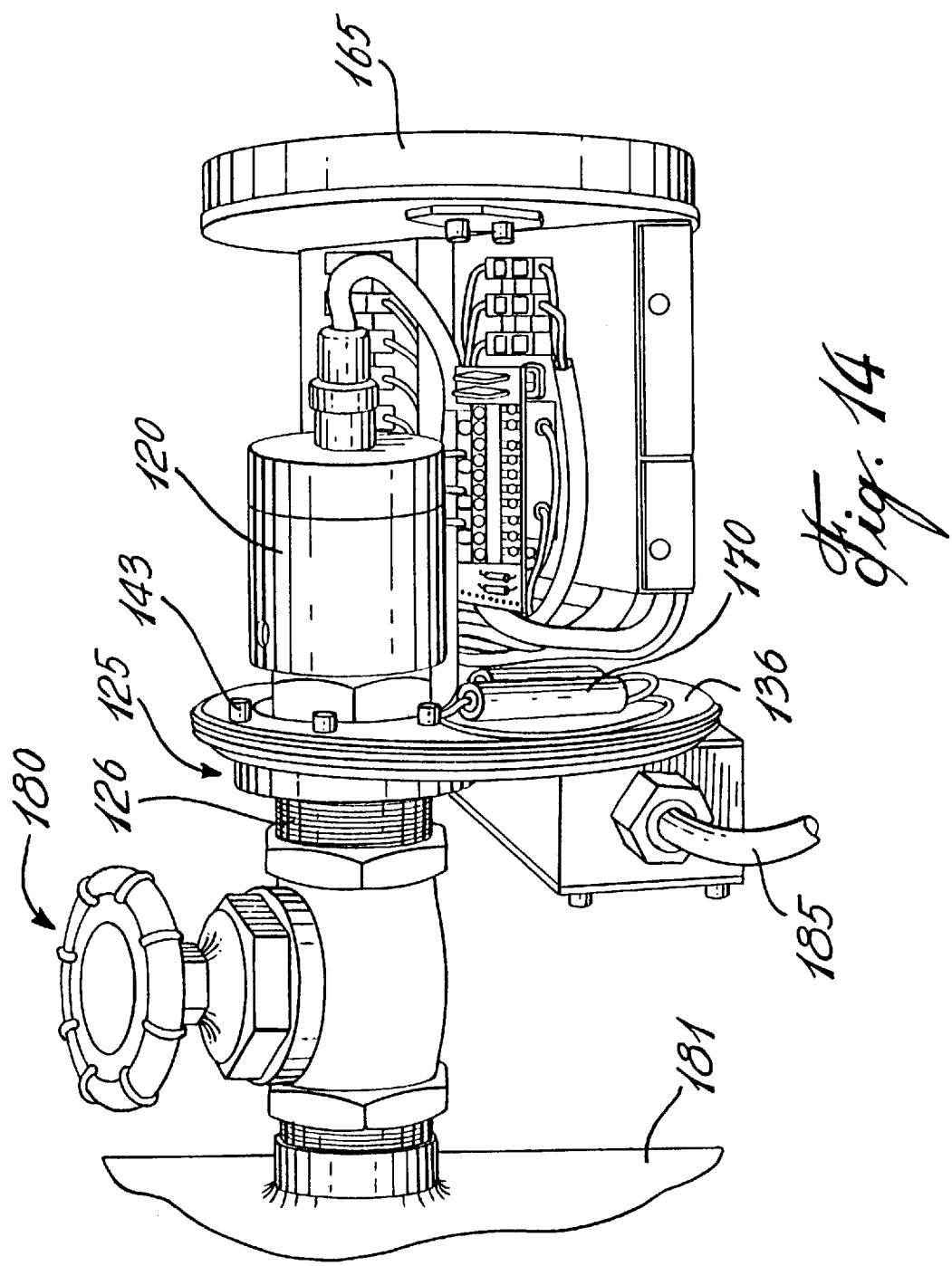

METHOD AND APPARATUS FOR THERMALLY INDUCING CIRCULATION OF FLUID BETWEEN THE INTERIOR OF A SYSTEM AND A FLUID POCKET ATTACHED THERETO

FIELD OF THE INVENTION

The present invention relates generally to a method and apparatus for inducing circulation of a fluid in an interior of a system between such interior and a fluid pocket. The present invention may in particular be exploited as part of a means for the monitoring (e.g. detection) of one or more substances in fluid insulated electrical equipment, e.g. to monitor incipient failure conditions. The present invention more particularly relates to an apparatus for monitoring (e.g. sampling and analysis of) a substance in a dielectric fluid whereby such fluid may be induced by convection to be displaced between the electrical system and the monitoring apparatus. The dielectric fluid may be a dielectric liquid (e.g. oil) or a dielectric gas.

The following will deal in particular with dielectric fluids and electrical systems. However, it is to be understood that this is done by way of example only. The invention is applicable to other types of fluid and systems.

BACKGROUND OF THE INVENTION

Electrical systems are well known in the art which use a dielectric fluid as an insulating substance; these systems include for example transformers, circuit breakers and the like.

It is known that, in the event of a disturbance or malfunction of an above mentioned type of device or system, the result may be the production of one or more undesired gases in the insulating fluid; this may occur for example if a device is working at too high a temperature or due to a high electrical discharge therein. Such conditions may also produce undesired moisture and/or one or more breakdown products in the insulating fluid. If such incorrect conditions are allowed to continue uncorrected, this may lead to irreparable damage to the electrical system. A timely (e.g. immediate) diagnosis of any such incorrect operation of an electrical apparatus is thus advantageous in order to be able to avoid irreparable harm to such a system.

Accordingly, various monitoring devices and systems have been proposed for the detection of any incipient failure conditions; such as for example any undesired increase of the concentration of a fault gas (e.g. a combustible gas such as for example, hydrogen gas, carbon monoxide gas, methane gas, ethane gas, ethylene gas, acetylene gas and the like), moisture (e.g. water), a breakdown product, contaminant substance, and/or the like contained (e.g. dissolved) in the insulating fluid.

Some such monitoring systems are, for example, described in Canadian Patent no. 1,054,223 (Bélanger), U.S. Pat. No. 4,112,737 (Morgan), U.S. Pat. No. 4,293,399 (Bélanger et al), U.S. Pat. No. 4,271,474 (Bélanger et al), U.S. Pat. No. 5,070,738 (Morgan) and U.S. Pat. No. 5,271,263 (Gibeault).

For example, U.S. Pat. No. 4,293,399 describes how the concentration of gaseous hydrogen dissolved in a fluid may be determined by a measure of an electric current generated by electro-chemical oxidation of the gaseous hydrogen at an electrode of detection. The prior art detecting and measuring device described in this U.S. patent comprises a polymeric membrane permeable to hydrogen gas for contact with a fluid containing dissolved hydrogen gas; an electrolyte capable of facilitating oxidation of the hydrogen gas diffused through the polymeric membrane at a first electrode and reduction of an oxygen-containing gas such as air at a second electrode; and a measuring device connected across the electrode for measuring the intensity of the electrical current generated by the electro-chemical reaction of oxidation of the hydrogen gas, this intensity being proportional to the concentration of hydrogen in the fluid.

It is advantageous for such monitoring (e.g. detection) devices, as described above, to be able to provide a timely and accurate diagnosis of the incorrect operation of systems such as, for example, transformers, circuit breakers, reactance or any electro-apparatuses using a dielectric fluid such as dielectric liquid (e.g. a dielectric oil) or a dielectric gas (e.g. $SF_6$ gas) as insulating substance.

A number of the above mentioned prior art monitoring devices or systems have the drawback that the sample received by the detector may not be uniform or representative of the fluid contained in the electrical system at a given moment in time. For example, in U.S. Pat. No. 4,293,399, the detector is attached to the wall of the electrical apparatus and the fluid must passively diffuse to that area to reach the detector. Such a passive sampling system has two inherent problems. Firstly, the sample that does reach the detector may not be uniform, and secondly if gases, moisture or breakdown products are introduced at some point in the system, which is remote from the detector, it may take considerable time before they will be detected.

A number of monitoring systems and devices have been proposed as solutions to the problems of passive sampling. Thus for example, U.S. Pat. Nos. 5,070,738 and 5,271,263 teach active sampling or detection devices and systems. The devices taught in these patents, exploit a mechanical pump for inducing the circulation of dielectric fluid between an electrical system and a detection member or element thereof. The presence of the mechanical pump, however, means that such a sampling system is susceptible to mechanical failure, i.e. due to the possibility that some moving part of the pump may fail.

Accordingly, it would, in general, be advantageous to have a means for inducing circulation of a fluid in an interior of a system between such interior and a fluid pocket without the need for a mechanism requiring moving mechanical parts, e.g. so as to facilitate the obtaining of a relatively representative fluid sample from a fluid pocket for analysis. It would be advantageous to have such a means which may be used with a broad range of fluids and/or systems so as to facilitate the taking of samples and/or monitoring of substance concentrations on a continuous and/or intermittent basis. It would also be advantageous if any analysis could be effected on location and/or at a remote analytic laboratory. It would in particular be advantageous to be able to facilitate analysis on location or at a site.

It would more particularly be advantageous to have a device which does not exploit a mechanical pump but which nevertheless facilitates the taking of a sample of fluid which may be relatively representative of the fluid in an electrical system.

It would also be advantageous to have a system which does not use a mechanical pump but which nevertheless, may provide a timely monitoring (e.g. detection) of a substance such as, for example, a fault gas, moisture, breakdown product and/or the like as mentioned herein.

It would additionally be advantageous to have an apparatus or device for inducing circulation which may be relatively easily installed onto an existing system and in particular to a single liquid access opening of such an system. It would more particularly be advantageous to have a monitoring (e.g. sampling and detecting) apparatus or device which may be relatively easily installed onto an existing electrical system and in particular to a single liquid access opening of such an electrical system. It would also be advantageous to have a means for inducing an exchange of fluid which would not require the introduction into the system of some sort of tubing, etc for withdrawal of fluid.

SUMMARY OF THE INVENTION

Accordingly, the present invention relates to thermal means for inducing circulation of a fluid, in an interior of a system, between such interior and a fluid pocket connected thereto. The fluid in the fluid pocket may in this manner be exchanged for fluid in the system. A sample, as desired, may be taken from the pocket which may thus be taken as representative of the fluid in the rest of the system. Such circulation may be induced in accordance with the present invention by adjusting or modulating the temperature of fluid in the fluid pocket either directly or indirectly so as to establish a temperature gradient between fluid in the pocket and fluid in the interior of the system in question, i.e. so as to establish a convection current between fluid in the fluid pocket and fluid in the system in the area about the access opening.

Thus, the present invention, in a general aspect, provides for a method for inducing circulation of a fluid, in an interior of a system, between said interior and a fluid pocket, said fluid pocket being in fluid communication with a fluid access opening of the system for fluid communication between the fluid pocket and the interior of the system, said method comprising modulating the temperature of a heat transfer element in thermal communication with fluid in said pocket, between a first temperature and a second temperature.

The fluid may be any fluid, e.g. the fluid may be a dielectric fluid as described herein, water etc.

In another aspect the present invention provides for an apparatus for inducing circulation of a fluid, in an interior of a system, between said interior and a fluid pocket, the apparatus comprising:

a) attachment means for attaching the apparatus to said system so as to define a housing, said housing defining a fluid pocket, said fluid pocket being in fluid communication with a fluid access opening of the system for fluid communication between the fluid pocket and said interior of the system, and b) heat transfer means comprising a heat transfer element configured for thermal communication with fluid in said pocket, said heat transfer means comprising temperature modulation means for modulating the temperature of the heat transfer element between a first temperature and a second temperature.

The present invention in further aspect provides for a combination comprising a system comprising a fluid in an interior thereof, said system comprising a fluid access opening for fluid communication with said interior of the system, and a component for inducing circulation of the fluid between said interior and a fluid pocket, said component comprising:

a) a housing, said housing defining a fluid pocket, said housing being attached to the said system such that the fluid pocket is in fluid communication with the fluid access opening for fluid communication between the fluid pocket and said interior of the system, and b) heat transfer means comprising a heat transfer element configured for thermal communication with fluid in said pocket, said heat transfer means comprising temperature modulation means for modulating the temperature of the heat transfer element between a first temperature and a second temperature.

In the context of the present invention the "interior" of a system in relation to the fluid is a reference to the portion of a system in which a fluid is contained for working purposes. In the context of an electrical transformer for example this will include the main body of the transformer, any heat radiating or cooling fin element for cooling the dielectric fluid by shedding heat to the ambient atmosphere as well as any other accessory body containing fluid and which is connected to the main body.

In accordance with the present invention, it is to be understood that the attachment of an apparatus for monitoring a substance may be a direct attachment or an indirect attachment. In the case of a direct attachment, the apparatus may, for example, be connected directly to an access opening by a wall component defining a fluid pocket component without any intervening tube or pipe like members, i.e. in this case the fluid pocket component defines the entire fluid pocket rather than just a part thereof as shall be described below; please see FIG. 2 of U.S. Pat. No. 4,293,399 for an example of a direct attachment to a system. In the case of an indirect attachment, the apparatus may, for example, be connected to a system via a valve as shall be discussed below; such connection will permit the easy removal of the apparatus from a system without, for example, the necessity of emptying the system or at least reducing the level of fluid in order to avoid spillage of fluid if for example the monitoring apparatus must be replaced or repaired. The valve in this later case, will define a part of the fluid pocket.

The heat transfer means may take on any desired or necessary form so long as the heat transfer element thereof may be in thermal communication with any fluid in the fluid pocket.

The heat transfer element itself may also take on any desired or necessary form. The heat transfer element may be an active one, i.e. wherein heat may be forced into or out of fluid in the fluid pocket. Heat may be transferred into fluid in a fluid pocket through the use of an electrically energisable heating element. Heat may be transferred out of fluid in a fluid pocket through the use of a refrigeration element. A heat transfer element may, if desired comprise a passive component i.e. wherein heat may be taken up from or shed to the ambient atmosphere depending on the temperature difference with the ambient air. A combination of such heat transfer scenarios may of course be used as desired or necessary.

Thus, for example, the heat transfer means may comprise a wall component which in turn defines a fluid pocket component and which is configured for thermal communication with any fluid therein, i.e. as the temperature of the wall component rises or falls heat is added to or taken away from any fluid in the fluid pocket component thereby facilitating the establishment of a convection current between fluid in the fluid pocket component and fluid in the system. The heat transfer means in this case may include heater element(s), e.g. electrical resistive heater element(s) which are in direct or indirect thermal contact or communication with the wall component or element for heating up the wall component. The temperature of the wall component may be actively controlled by adjusting the electric current being passed through the electrical resistive heater element(s)

whereby the temperature of the fluid may in turn be raised; lowering of the temperature of the wall component may be achieved by allowing the wall component to air cool i.e. radiate heat to the atmosphere and thus lead to cooling of the fluid.

Alternatively, the heat transfer element may, for example, comprise an electrical resistive heating element in the form of a rod which is able to project into fluid in the fluid pocket.

In accordance with the present invention the heat transfer means may comprise temperature modulation means for modulating the temperature of the heat transfer element between a first temperature and a second temperature i.e. a second temperature which is different (e.g. greater) than said first temperature. Since the heat transfer element of the heat transfer means is able to be thermally connected to the fluid, (i.e. is able to be in heat transfer relation thereto) the fluid may likewise pass between a first temperature and a second temperature such that a changing temperature differential or gradient may be obtained between fluid in the fluid pocket and the system, e.g. between fluid in the fluid pocket and fluid at the mouth of the fluid access opening into the system.

In other words, the heat transfer means is intended to be able to oscillate the temperature of the heat transfer element between two temperatures. Thus, when the heat transfer element is in thermal communication with the fluid such alternating temperature of the heat transfer element facilitates the establishment of a thermal temperature gradient and hence a fluid convection current whereby a fluid (e.g. a dielectric fluid) may pass between the monitoring device and the system being monitored. In effect the heat transfer means may be considered to be a thermal pumping means whereby fluid may effectively be drawn, for example, into a monitoring device or apparatus from the system and then be expelled from such device back into the system.

As mentioned the heat transfer means may take on any desired or necessary form. It is to be constructed keeping in mind that it is intended to manipulate the temperature difference of the heat transfer element. The modulation means is to be chosen on the basis that the temperature difference (i.e. the amplitude) as well as the period (or rate of temperature change) are to be able to be set such that the fluid pocket (e.g. fluid pocket component) is able to be provided with a representative sample of fluid under the working conditions of the system. The modulation may be such as to give the temperature variation any suitable or desired wave shape. The particular wave shape for any particular system may simply be established by appropriate empirical experiments in any particular case.

Any suitable means may be used for the purpose of modulating the temperature of the heat transfer element. The heat transfer means may for example include a suitable heat sensor in thermal communication with the wall component or element defining a fluid pocket component. The heat sensor also be may be connected to suitable controller means. The controller means may be connected directly or indirectly to an electrical power source for activation and deactivation of for example a thermal heater resistor element as mentioned above or a refrigeration or cooler element. The controller may be configured to compare a modulating (i.e. changing) temperature reference signal from a reference signal generator with the temperature signal from the heat sensor and based on any difference between such signals either increase or decrease the amount of energy being sent to the heater elements and or cooler elements. If desired a suitable microprocessor means and suitable software may be used to carry out the function of the controller and signal generator.

The heat transfer means may for example comprise temperature modulation means for modulating the temperature difference between the first temperature and the second temperature such that there is about a temperature difference of for example 20° C. or less (e.g. 10° C. or less, 5° C., etc.). In any event, the temperature difference between the first temperature and the second temperature may be larger if desired or necessary. The actual temperatures themselves will depend on the working temperature of the electrical system and any monitoring (e.g. sampling and analysing) means. The temperature of a heat transfer element may for example be modulated between a first ambient temperature and a second temperature greater than said ambient temperature.

An apparatus (i.e. an apparatus not yet connected to a system), in accordance with the present invention, may be provided with a fluid pocket component defined by a wall component. The wall component may be connected to the access opening of a system directly or if so desired it may be connected indirectly by any suitable fluid conduit means. The conduit means may for example be as simple as a valve or may include additional tubing or piping. In such case the additional conduit means along with the wall component will define the overall fluid pocket connected to a system. It is to be understood of course that an apparatus for inducing a convection current (e.g. a monitoring apparatus as described herein) may be releasably connected to a system so as to facilitate its replacement and repair. Alternatively, such an apparatus may be fixed in a more or less permanent manner to a system such as for example by welding; in this latter case it will of course prove more difficult to replace or repair the apparatus.

With respect to an apparatus itself, if desired or necessary, the apparatus may include a valve component which forms part of the wall component and thus partially defines the fluid pocket component. The valve component may be configured for a more or less permanent attachment to the rest of the apparatus or else for a releaseable connection thereto; advantageously, the rest of the apparatus may be releasably connected to such valve component so as to facilitate repair and/or replacement.

In the context of a combination as described herein, The fluid conduit means and the wall component may, for example, be so configured as to define an essentially straight passageway.

The passageway may be disposed or attached to the system so as to be horizontal. A passageway may also be disposed so as to be inclined downwardly from the access opening. Alternatively, it may be disposed so as to have a vertical component e.g. so as to have an upward inclination. In any of these cases, the first and second temperatures are, as may be appreciated from the above, chosen so as to be able to set up a changing or alternating temperature gradient between fluid in the fluid pocket and fluid in said system interior which favours a fluid convection current flow between fluid in the system in the area of the opening leading to the system interior and fluid in the fluid pocket.

For example, if a fluid pocket is disposed so as to extend vertically above the access opening leading to the system interior, it may be desired to keep the temperature of the fluid in the fluid pocket at two temperatures both of which are below the temperature of the fluid in the area of the opening. In this latter case, it should be born in mind that if the temperature of the fluid in the fluid pocket is above that of the fluid in the interior of the system no convection current will be established; the reverse is true if the pocket extends vertically below the access opening. Alternatively, if the passageway is horizontally disposed then one temperature may be above and the other below the temperature of the fluid in the area of the opening leading to the system interior.

The size and configuration of the above described passageway should also be chosen with a view to facilitating the exchange of fluid in the fluid pocket by thermal means. The passageway may, for example, but not restricted to, have a minimum diameter d and a length l wherein the ratio of l to d is 6 to 1 or less; the minimum diameter being the size of the smallest restriction in an otherwise large diameter passageway. Other ratios could of course be used keeping the above in mind. The passage way may have an essentially constant diameter over its entire length. The passageway may alternatively have a diameter which varies over its length; in this case the minimum diameter is the diameter used for the above ratio. In any event, the diameter d and length l may have values providing other ratios, keeping in mind the purpose of the passageway, i.e. to facilitate fluid flow.

The passageway need not necessarily be straight; it may take on other configurations keeping in mind, however, that the configuration is to be chosen on the basis of facilitating an exchange of fluid in the pocket and a system by thermal means as discussed herein.

As may be appreciated, since the pumping action is induced by heat transfer it is not necessary to have a tubing element project into the system as suggested in some of the above mentioned prior art.

The fluid may be any fluid for which a convection current may be desired to be established by setting up a temperature gradient between fluid in a system (e.g. being checked) and fluid in a fluid pocket as described herein, e.g. the fluid may be a dielectric fluid as described herein, water, etc.

The present invention also relates, in a particular aspect, to an apparatus, device, system or method which may be used to monitor one or more substances in a fluid for whatever desired reason; i.e. to monitor the presence, concentration, etc. of such a substance over time. Thus the above mentioned method for inducing circulation of a fluid may include a step for monitoring the presence of a substance in fluid in a fluid pocket. The above described apparatus or combination(s) may include means for monitoring a substance in fluid in a fluid pocket.

It is to be understood herein that the word "monitoring" includes, but is not limited to, continuous measurement of a substance, intermittent measurement of a substance, removal of a fluid sample for analysis of a substance (e.g. for on site analysis or analysis at a remote site (e.g. laboratory)), etc.

The present invention also relates, in a more particular aspect, to an apparatus, device, system or method which may be used to monitor one or more substances in a fluid which are indicative of incipient failure conditions in fluid insulated electrical equipment or systems; i.e. to monitor the presence, concentration, etc of such a substance over time. The apparatus or system may, for example, be used to detect the presence of substances contained in the insulating fluid of transformers such as for example fault gases, moisture or breakdown products (see above).

The present invention with respect to this other particular aspect relates to an apparatus or combination wherein a dielectric fluid (e.g. liquid or gas) may be monitored (e.g. sampled and tested) by being withdrawn from and returned to the interior of an electrical system by use of a heat transfer means which is in thermal communication with the fluid in a fluid pocket as discussed herein.

Thus, the present invention, also provides in an apparatus for monitoring a substance in a dielectric fluid, said fluid being in an interior of an electrical system, the apparatus comprising:
  a) attachment means for attaching the apparatus to said electrical system so as to define a housing, said housing defining a fluid pocket, said fluid pocket being in fluid communication with a dielectric fluid access opening of the electrical system for fluid communication between the fluid pocket and said interior of the electrical system, and
  b) means for monitoring said substance in dielectric fluid in said fluid pocket,
the improvement wherein said apparatus comprises heat transfer means comprising a heat transfer element configured for thermal communication with dielectric fluid in said pocket, said heat transfer means comprising temperature modulation means for modulating the temperature of the heat transfer element between a first temperature and a second temperature.

In accordance with the present invention, as mentioned the attachment means may be configured for connecting the fluid pocket to a single dielectric liquid access opening of an electrical system.

The heat transfer means as mentioned above may comprise a wall element or component which defines a fluid pocket component.

Accordingly, the present invention also provides in an apparatus for monitoring a substance in a dielectric liquid, said liquid being in an interior of an electrical system, the apparatus comprising:
  a) a wall component defining a fluid pocket component, said wall component being configured for thermal communication with dielectric liquid in said pocket component,
  b) attachment means for attaching the apparatus to said electrical system so as to define a housing, said housing comprising said wall component and defining a fluid pocket, said fluid pocket being in fluid communication with a dielectric liquid access opening of the electrical system for liquid communication between the fluid pocket and said interior of the electrical system, said fluid pocket comprising said fluid pocket component, and
  c) means for monitoring said substance in dielectric liquid in said fluid pocket,
the improvement wherein said apparatus comprises heat transfer means, said heat transfer means comprising said wall component, said heat transfer means comprising temperature modulation means for modulating the temperature of the wall component between a first temperature and a second temperature.

In accordance with a further aspect, the present invention provides, in a combination comprising
  an electrical system comprising a dielectric fluid in an interior thereof, said electrical system comprising a fluid access opening for fluid communication with said interior of the electrical system, and
  a monitoring component for monitoring a substance in the dielectric fluid, the monitoring component comprising:
    a) a housing, said housing defining a fluid pocket, said housing being attached to the electrical system such that the fluid pocket is in fluid communication with the fluid access opening for fluid communication between the fluid pocket and said interior of the electrical system, and b) means for monitoring said substance in dielectric fluid in said fluid pocket, the improvement wherein said monitoring component comprises heat transfer means comprising a heat transfer element configured for thermal communication with dielectric fluid in said fluid pocket, said heat transfer means comprising temperature modulation means for modulating the temperature of the heat transfer element between a first temperature and a second temperature.

The present invention also provides in a combination comprising an electrical system comprising a dielectric liquid in an interior thereof, said electrical system comprising a liquid access opening for liquid communication with said interior of the electrical system, and a monitoring component for monitoring a substance in the dielectric liquid, the monitoring component comprising:

a) a housing, said housing comprising a wall component, said housing defining a fluid pocket, said housing being attached to the electrical system such that said fluid pocket is in liquid communication with said liquid access opening for liquid communication between the fluid pocket and said interior of the electrical system, said wall component defining a fluid pocket component, said fluid pocket comprising said fluid pocket component, said wall component being configured for thermal communication with dielectric liquid in said fluid pocket component, and b) means for monitoring said substance in dielectric liquid in said fluid pocket, the improvement wherein said monitoring component comprises heat transfer means, said heat transfer means comprising said wall component and temperature modulation means for modulating the temperature of the wall component between a first temperature and a second temperature.

In accordance with the present invention the apparatus may be connected to the access opening by fluid conduit means, the fluid conduit means and the wall element defining an essentially straight horizontal passageway.

Alternatively, in accordance with the present invention the apparatus may be connected to the access opening by fluid conduit means, the fluid conduit means and the wall element defining an essentially straight passageway inclined downwardly from the access opening.

The passageway may as desired or necessary be other than straight and may for example incline upwards, keeping in mind of course the purpose of the passageway, i.e. to facilitate fluid flow.

The substance to be monitored (e.g. detected) may, for example, comprise a member of the group comprising a fault gas (e.g. a combustion gas such as for example, hydrogen gas), moisture (e.g. water), and/or a breakdown product.

The detection or monitoring means may take on any desired or necessary form. The monitoring means may, for example, comprise an electrochemical detector, a semiconductor detector, a metal oxide detector, a capacitive detector (e.g. for water), a chromatograph (e.g. a gas chromatograph), a spectrograph (e.g. I.R. spectrophotometer), and the like.

In accordance with the present invention, the monitoring means may take on the configuration of the detector device described in U.S. Pat. No. 4,293,399. Thus the monitoring means may, for example, comprise an isolation member for isolating the substance from the dielectric liquid, the member being disposed for contacting dielectric liquid in said pocket. The isolation member may, for example, comprise a membrane, permeable to a said substance and impermeable to said dielectric liquid, the membrane being disposed for contacting, on one side thereof, dielectric liquid in said pocket; see for example the above referred to U.S. Pat. No. 4,293,399.

The surface of the isolation member of a detector which contacts the fluid may be disposed perpendicularly to the flow of the fluid in the fluid pocket. This surface is in any event located so as to facilitate isolation of the substance or substances being monitored in a relatively representative fashion.

The present invention is relatively easy to adapt to an existing electrical system as it requires only one inlet/outlet port to be attached to the electrical system. The oscillating thermal pumping action can facilitate the continuous and uniform flow of the fluid (e.g. liquid) into and out of a sampling and detection apparatus.

In the drawings which illustrate example embodiments of the invention:

FIG. 8b is a rear view of the device shown in FIG. 8a;

FIG. 9b is a side view of the attachment element of FIG. 9a;

FIG. 10b is a side view of the attachment element of FIG. 10a;

FIG. 12 is a schematic side view of the heating plate member of FIG. 11 wherein an extension attachment element of FIG. 9a is shown in the process of being attached thereto;

FIG. 13 is a top schematic view of an example apparatus in accordance with the present invention wherein the outer casing is removed;

FIG. 14 is a schematic perspective view of an example monitoring apparatus in accordance with the present invention attached to a gate valve providing access to the interior of an electrical transformer, the main body of the transformer not being shown and the outer casing being removed;

Figure 1:
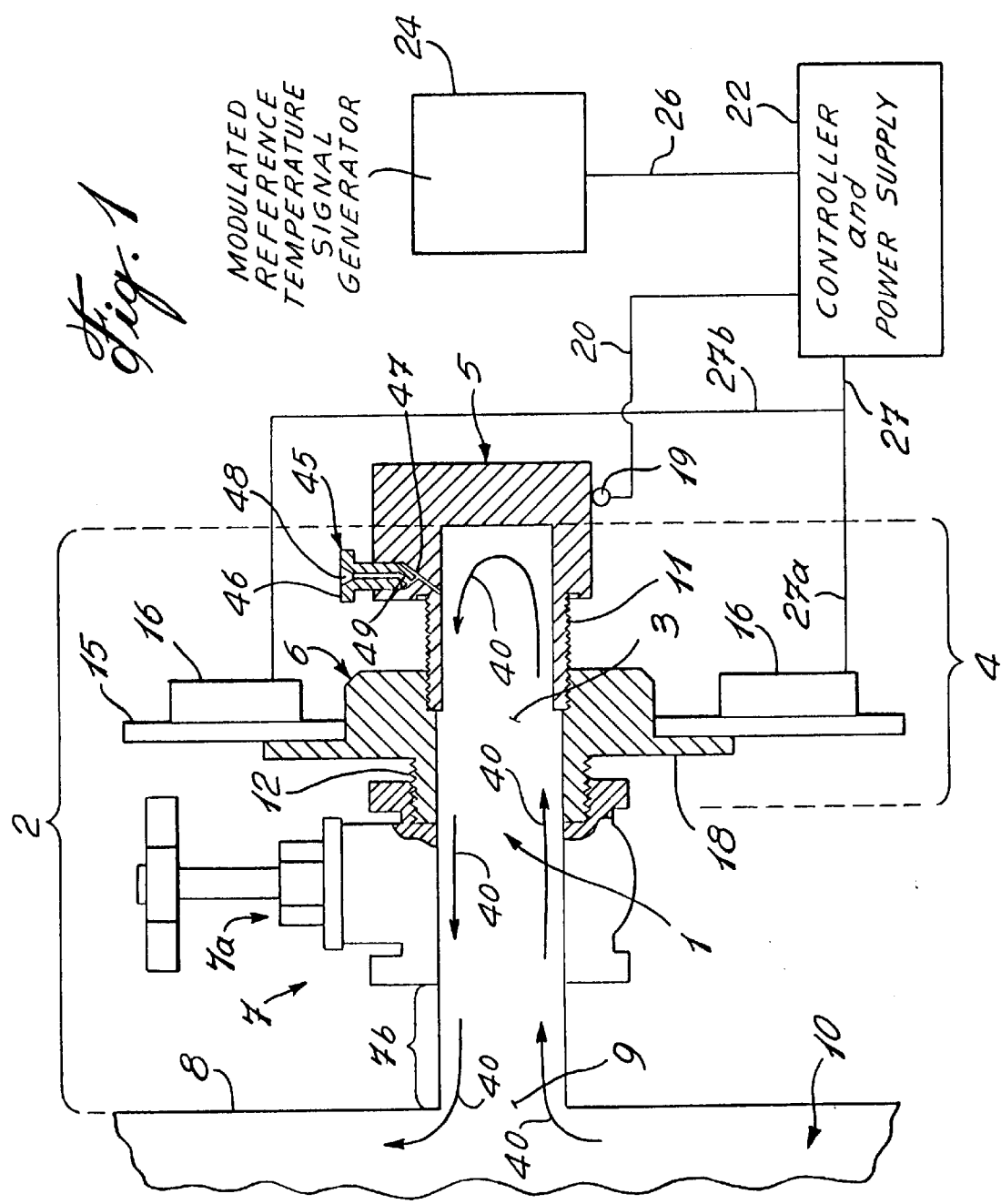
FIG. 1 is a schematic illustration of an example current inducing apparatus in accordance with the present invention attached to a valve providing access to the interior of an electrical transformer, the main body of the transformer not being shown.

Referring to FIG. 1, this figure illustrates in a schematic and block fashion an example of an apparatus for thermally inducing circulation of a fluid between a main body of fluid and fluid in a fluid pocket (e.g. a sampling fluid pocket). The apparatus is shown as being connected to an electrical transformer system, i.e this figures shows a combination in accordance with the present invention. Only a portion of the wall of the transformer in the immediate vicinity of the apparatus is shown for purposes of illustration.

The fluid pocket is indicated generally by the reference numeral 1; in the example shown the overall fluid pocket is configured as a horizontal passageway; as mentioned above such a passageway may be at a different inclination e.g. be inclined downwardly. The fluid pocket 1 has an overall length indicated by the reference numeral 2. The fluid pocket 1 comprises a fluid pocket component indicated generally by the reference numeral 3. The fluid pocket component 3 has an overall length indicated generally by the reference numeral 4. The fluid pocket 1 is defined by a housing which itself is defined by and comprises an end cap component 5, an extension attachment member 6 and a valve component 7. The cap component 5 and the extension attachment element 6 together define a wall component which defines the fluid pocket component 3.

The valve component 7 is attached to the transformer about the fluid access opening 9. The valve component 7 comprises a valve element 7a. The valve element 7a may for example comprises a gate valve or any other suitable type of valve. The valve component 7 also includes a small conduit member 7b which in the embodiment shown is fixed to the wall 8 of the transformer in a more or less permanent fashion (e.g. by welding). The valve element 7a is attached in releasable screw fashion to the conduit element 7b. The valve component 7 as shown is in a full open configuration so as to allow for fluid communication between the main body 10 of dielectric fluid (which is in the interior of the transformer) and the fluid pocket 1 through the access opening 9.

The end cap 5 has an exterior screw threaded surface 11; the extension element 6 has a corresponding inner screw thread surface whereby the end cap is attached to the extension element 6 in fluid tight and releasable fashion. The extension element 6 also has an outer screw threaded surface portion 12 engaging inner screw threads of the valve component 7 for fluid tight and releasable attachment thereto.

As may be surmised from (FIG. 1, the apparatus for inducing fluid circulation comprises the end cap component 5, the extension element 6 as well as the heat transfer components which shall be described below. The apparatus may be separated from the transformer by closing off the valve component 7 (i.e. to prevent spillage of fluid in the interior of the transformer) and then unscrewing the apparatus from the valve component 7, i.e. by unscrewing the extension element 6 from the valve component 7.

The apparatus for inducing fluid circulation includes a heat transfer plate member 15 and heater elements 16 (i.e. electric heater elements). The plate member 15 as well as the end cap member 5 and the extension attachment element 6 are made of a heat conducting material such as for example a metal substance such as brass. The plate member 15 is attached to the extension attachment element 6 such that it abuts the extension element 6 and in particular abuts the flange element 18 of the extension attachment element 6 so as to facilitate heat transfer there between. The heater elements 16 are likewise in abutting contact with the plate member 15 such that as the heater elements 16 are energised and become hot they transfer heat to the plate member 15 which in turn passes on heat to the extension attachment element 6. As the temperature of the extension attachment element 6 increases in this fashion it will also in turn pass on heat to any fluid in the fluid pocket component which is in contact with the inner wall surface of the above mentioned wall component of the housing.

For illustration purposes the apparatus is shown as having a temperature sensor 19 which is in thermal communication with the end cap component 5. The temperature sensor 19 is configured to generate a signal reflecting the temperature of the end cap. The temperature signal is sent via line 20 to the controller 22. The end cap component 5 is in abutting thermal communication with the extension attachment element 6. Thus any change (e.g. increase) in temperature of the extension attachment element 6 will induce a change in temperature of the end cap 5. Such a change in temperature will be reflected in the changing temperature signal sent to the controller 22. The controller 22 also has means for controlling a power source for energisation of the heater elements 16, i.e. to have the heater elements give off heat. The power source may be any source of electrical power.

The apparatus also has a passive cooling function. The cooling function of the apparatus exploits the transfer of heat into the ambient air contacting the various elements of the housing; during cooling the heating function of the heater elements 16 is either completely shut off or shut off in a controlled reduction or decreasing fashion, e.g. the energisation of the heaters is stopped and/or reduced. As air in contact with the housing elements takes up heat therefrom the housing is allowed to cool thereby; e.g. the extension attachment element 6 is air cooled to lower its temperature and in consequence the temperature of fluid in contact therewith in the fluid pocket component.

The temperature modulation means of the illustrated apparatus comprises a (variable) means 24 for generating a modulated (i.e. changing) temperature reference signal which is sent along line 26 to the controller 22. The controller 22 is configured to compare the reference signal with the temperature signal and based on any difference between such signals will either increase or decrease the amount of energy being sent to the heater elements 16 via line 27 (i.e. lines 27a and 27b), decreasing or stopping the energisation of the heater elements 16 will allow air cooling of the wall component and hence the fluid in the fluid pocket component.

Figure 2:
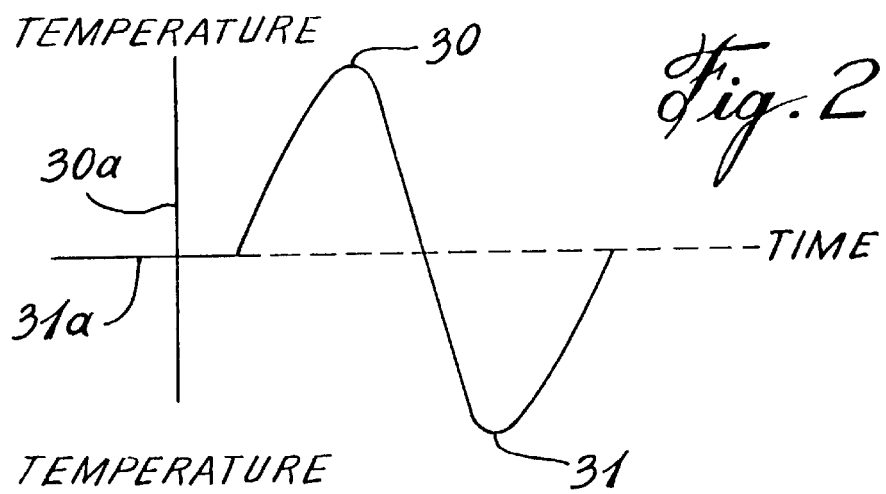
FIG. 2 illustrates an example sinusoidal waveform for a modulated reference temperature signal for changing the temperature profile of a heat transfer element.
Figure 3:
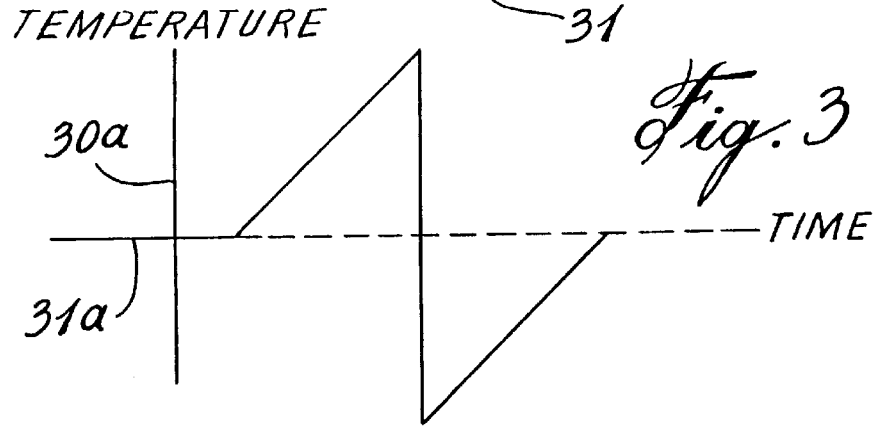
FIG. 3 illustrates an example sawtooth waveform for a modulated reference temperature signal for changing the temperature profile of a heat transfer element.
Figure 3A:
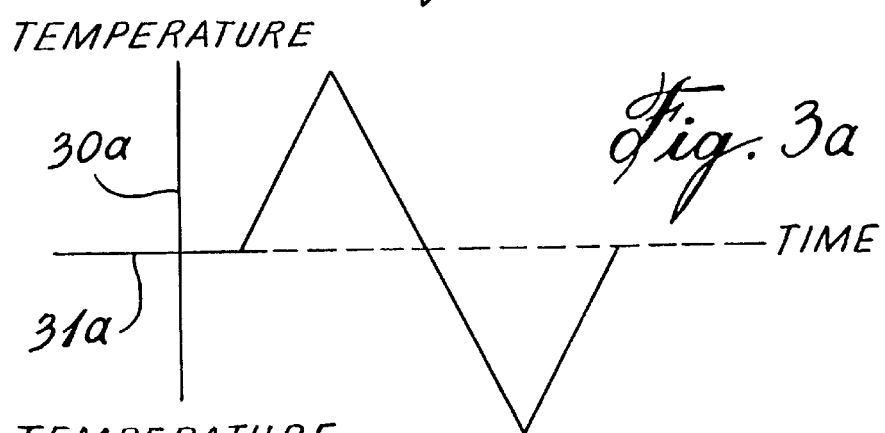
FIG. 3a illustrates another example triangle waveform for a modulated reference temperature signal for changing the temperature profile of a heat transfer element.
Figure 4:
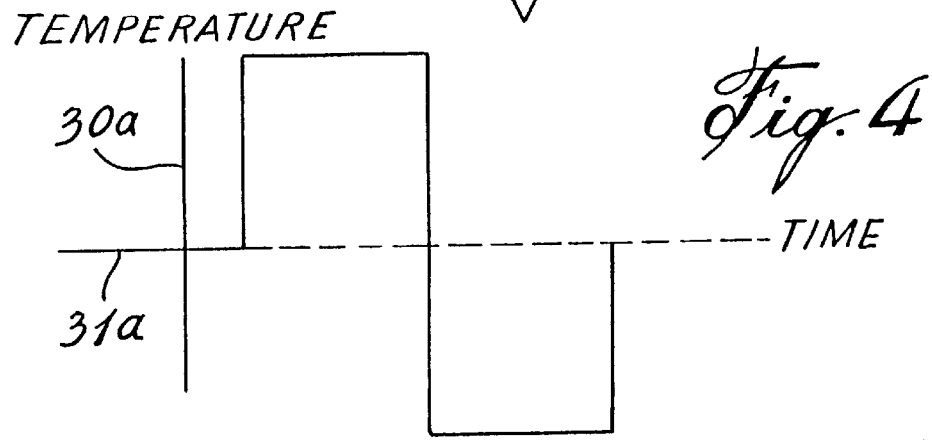
FIG. 4 illustrates an example square waveform for a modulated reference temperature signal for changing temperature profile of a heat transfer element.

The modulated reference temperature signal may take on any suitable form. FIGS. 2, 3, 3a and 4 show example modulated reference signals. Referring to FIG. 2, this figure shows a single cycle of a sine wave. In the case where the temperature of the fluid, in the system, adjacent the access opening 9 is about 28° to 32° C. and the ambient temperature is about 20° C., the sine wave may for example have an amplitude of 20° C., e.g. the temperature reference signal may vary for 10° C. about a median reference temperature of 30° C. The period of the sine wave may, for example, be two hours. Thus, for example, referring to FIG. 2, after one-half hour the reference temperature signal at the sinusoidal peak 30 is set at 40° C.; after one hour (i.e. after a half cycle) the reference temperature signal is set at 30° C.; and after one and a half hours the reference temperature signal is set at the sinusoidal trough 31 at 20° C. (i.e. at or near ambient temperature). During the first half cycle heating of fluid in the fluid pocket is favoured while during the last half cycle cooling of the fluid in the pocket is favoured.

In FIGS. 2, 3, 3a, and 4 the abscissa 30a is temperature and the ordinate 31a is time.

Referring to FIG. 1, for the example reference temperature signal changes given above, during the first half of the reference signal cycle the flow of fluid through the fluid pocket will, it is believed, flow in the direction of the arrows 40; during the second half (i.e. trough side) of the reference signal cycle the fluid flow will, it is believed, occur in the direction opposite to that of the arrows 40.

Any known electronic circuits may be used for the controller and for the temperature reference signal generator. The function of the controller and the temperature reference signal generator may, for example, if desired, be performed by using a suitable microprocessor and suitable software; the microprocessor of course being suitable connected to the temperature sensor 19 and an electrical power source for energisation of the heater elements 16.

Referring back to FIG. 1, as may be apparent from the above, the example apparatus for inducing fluid flow, as mentioned above, comprises the end cap 5 and the extension attachment element 6; it also includes a heat transfer means which comprises a heat transfer element comprising the extension attachment element 6 and the heat transfer plate member 15. The heat transfer means also includes a temperature modulation means which comprises the above mentioned heater elements 16, the temperature sensor 19, the temperature reference signal generator 24, and the controller (and power source) 22.

As may be appreciated, the temperature of the extension attachment element 6 may be raised so as to result in an increase in the temperature of the fluid in the fluid pocket component. If the temperature of the fluid in the fluid pocket component is able to be raised higher than the temperature of the fluid at the access opening 9 a temperature gradient will be established. Similarly, a temperature gradient may be established if the temperature of the fluid in the fluid pocket is able to be lowered lower than the temperature of the fluid at the access opening 9.

The apparatus shown in FIG. 1 has means for removing a fluid sample from the fluid pocket e.g. for analysis.

The end cap 5 is provided with means for mechanically drawing a sample of the fluid in the fluid pocket component out for analysis either on the spot or at a remote location. The end cap 5 has a sample collector noted generally by the reference numeral 45. The sample collector includes a rotatable valve 46 inserted into a threaded opening which is able to communicate with the fluid pocket by means of a small connecting channel 47. The valve 46 has an open ended channel 48 with an open end 49. Rotation of the valve 4 until the open end 49 of channel 48 communicates with the channel 47 allows for the withdrawal of fluid, e.g. by a syringe like device. In the configuration shown the valve 46 may also be used as a bleed valve for the escape of gas from the fluid pocket.

Figure 5:
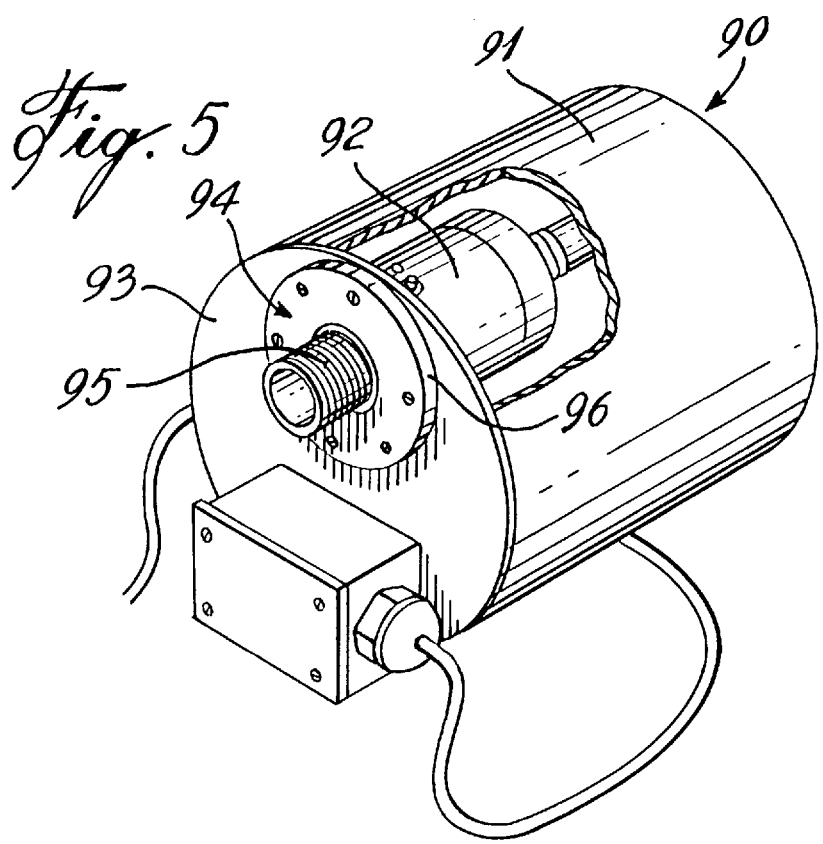
FIG. 5 is a schematic representation of an example monitoring apparatus in accordance with the present invention.

Referring to FIG. 5, this figure schematically shows an example of a monitoring apparatus 90 in accordance with the present invention. The apparatus 90 has an outer casing 91 which is partially cut away so as to reveal the detector element 92. The detector 92 is configured in any known manner to measure, for example, the concentration of combustible gas such as described above (for example, hydrogen gas, carbon monoxide, ethylene, acetylene, etc.) dissolved in a dielectric fluid. The detector 92 may for example be obtained from Syprotec Inc, Montreal Quebec, Canada under its trade mark HYDRAN. The apparatus 90 has a heat transfer plate member 93. The apparatus 90 also has an extension attachment element 94. The attachment element 94 has an outer threaded surface portion 95 for attaching the apparatus for example to an access valve of an electric transformer. The attachment element 94 also has a flange element 96. The flange element 96 is attached by screw or bolt members to the heat transfer plate member 93.

Figure 6:
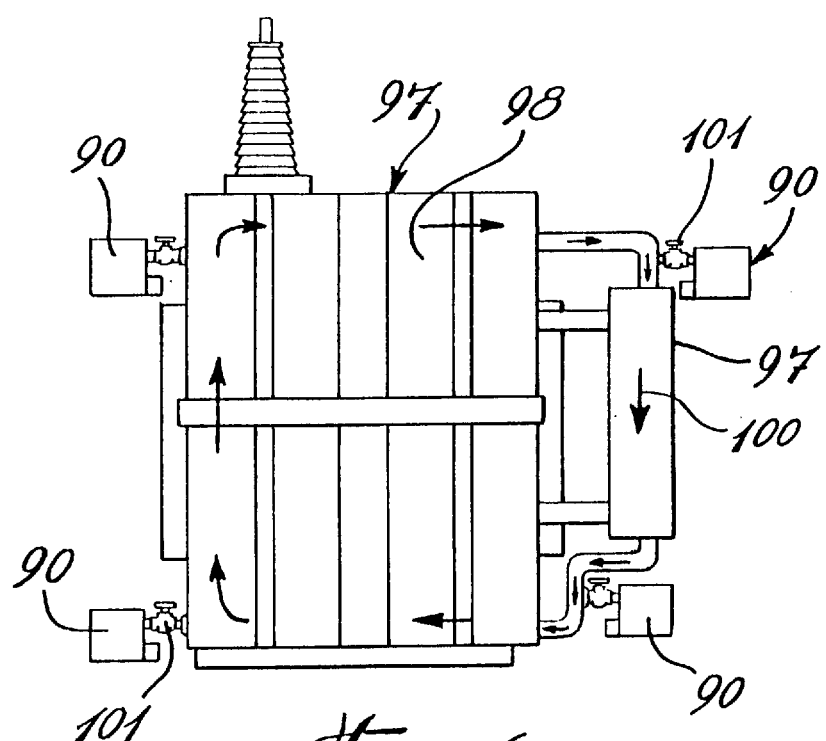
FIG. 6 is a schematic illustration of examples of various points of attachment of a monitoring apparatus of the present invention to an electrical transformer so as to form a combination as described herein.

FIG. 6 illustrates a combination in accordance with the present invention. The combination includes a transformer 97 and a plurality of monitoring apparati 90. A dielectric fluid (e.g. liquid) is disposed in the interior of the system and circulates between the main body 98 of the transformer 97 and the heat dissipation fin component 99 thereof; the circulation of the fluid is indicated generally by arrows two of which are designated with the reference numeral 100. As may be seen the monitoring apparati 90 may be connected indirectly to the transformer by valves two of which are designated by the reference numeral 101. Four apparati 90 are shown only for the purpose of illustrating example positions or connections spots of such an apparatus to the transformer 97; other positions may of course be used.

Figure 7:
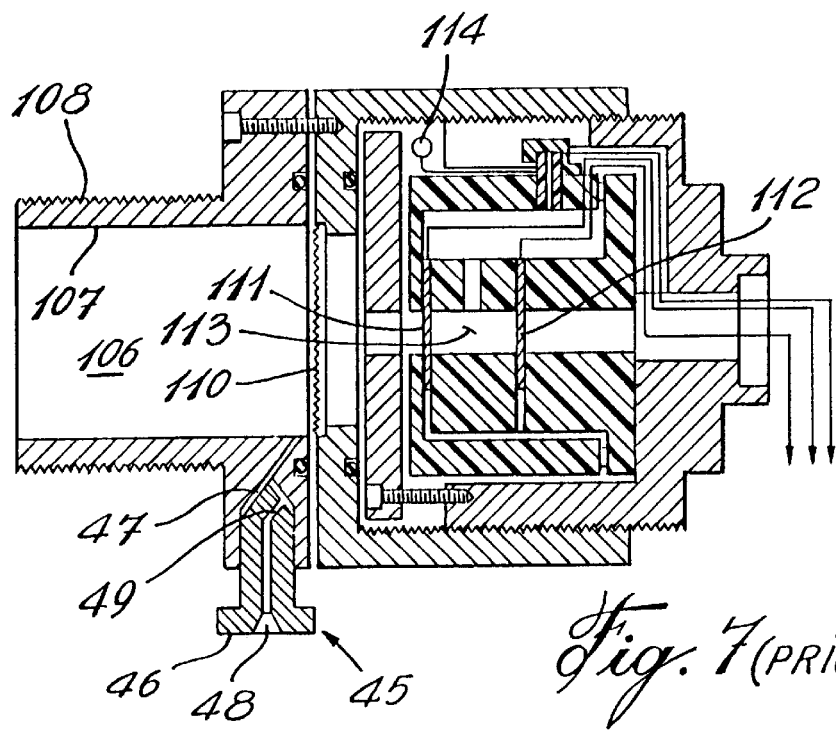
FIG. 7 is a longitudinal cross sectional view of a known detection device.

Referring to FIG. 7, this figure illustrates a known configuration for a detector for measuring hydrogen gas in a dielectric fluid; this configuration is described in U.S. Pat. No. 4,293,399 the entire contents of which are incorporated herein by reference. The detector has a fluid pocket element or component 106 defined by cylindrical wall element 107. The wall element 107 is provide with a screw threaded outer surface 108 which may be used to attach the detector to an extension attachment element as described herein below. The detector has a polymeric membrane 110 which is permeable to hydrogen gas, a detection electrode 111 at which occurs the oxidation of hydrogen diffused through the membrane 110 and an electrode 112 in contact with an oxygen containing gas such as air at which occurs the reduction of the oxygen contained in the gas and an electrolyte 113 for facilitating the oxidation-reduction reactions. The device is provided with appropriate wires for connecting the electrodes to any suitable or known measuring circuit (not shown) for measuring the intensity of current generated by the detector and hence the hydrogen gas concentration of any dielectric fluid in the fluid pocket element 106. The detector structure shown in U.S. Pat. No. 4,293,399 may be adapted to measure other combustible gases mentioned above (e.g. carbon monoxide, ethylene, acetylene, etc.)

The detector shown in FIG. 7 also is provided with a thermocouple or thermistor means 114 for use in measuring the temperature of the device in the vicinity of the wall element 107, i.e. to obtain an indication of the temperature of the wall element 107 (see also element 19 of FIG. 1). The detector is also provided with appropriate wiring for connecting the thermistor element 114 to any suitable or known measuring means (not shown) for providing a signal indicative of the temperature of the wall element 106.

In FIG. 7, the reference numerals 45, 46, 47, 48 and 49 designate the same elements of the sample collector as shown with respect to FIG. 1.

Figure 8A:
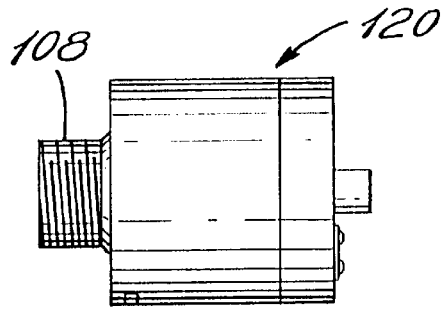
FIG. 8a is a longitudinal side view of an example detection device.
Figure 8B:
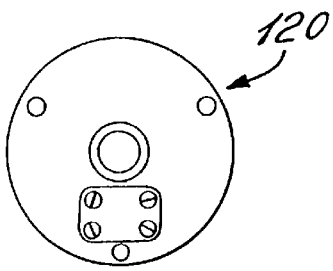

Turning to FIGS. 8a and 8b these figures illustrate a hydrogen gas detector 120 having an internal structure the same as the detector shown in FIG. 7; accordingly hereinafter the same reference numerals mentioned in FIG. 7 will be used to designate common elements. The detector 120 has an attachment element comprising outer thread surface 108.

Figure 9A:
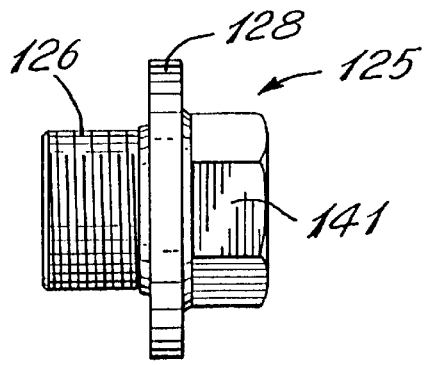
FIG. 9a is a side view of an example extension attachment element for attaching a detection device as shown in FIG. 8a to a heat transfer plate member for thermal communication thereto.
Figure 9B:
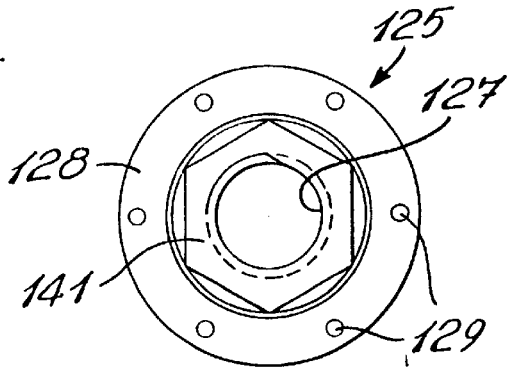

FIGS. 9a and 9b illustrate an example extension attachment element 125. The attachment element 125 has an outer threaded surface portion 126 and an inner threaded surface portion 127. The outer threaded surface portion 126 is configured for screw attachment with for example a valve element. The inner threaded surface is configured for engaging the outer threaded surface 108 of the detector 120. The extension attachment element 125 is also provided with means for attachment to a heat transfer plate member. In this respect the attachment element 125 is provided with an attachment flange 128; the attachment flange 128 is provided with screw threaded openings for engaging screw or bolt means for fixing the attachment element 125 to a heat transfer plate member. When the attachment element 125 is screw attached to the detector 120 by threaded surface 108, the fluid pocket element or component thereof is effectively lengthened.

Figure 10A:
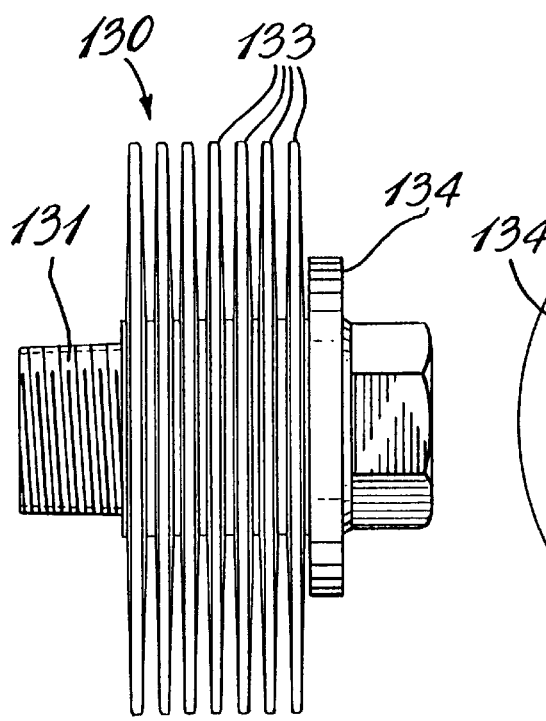
FIG. 10a is a side view of an example of an alternate extension attachment element for attaching a detection device as shown in FIG. 8a to a heating plate member for thermal communication thereto, the attachment element being provided with heat dissipation fins.
Figure 10B:
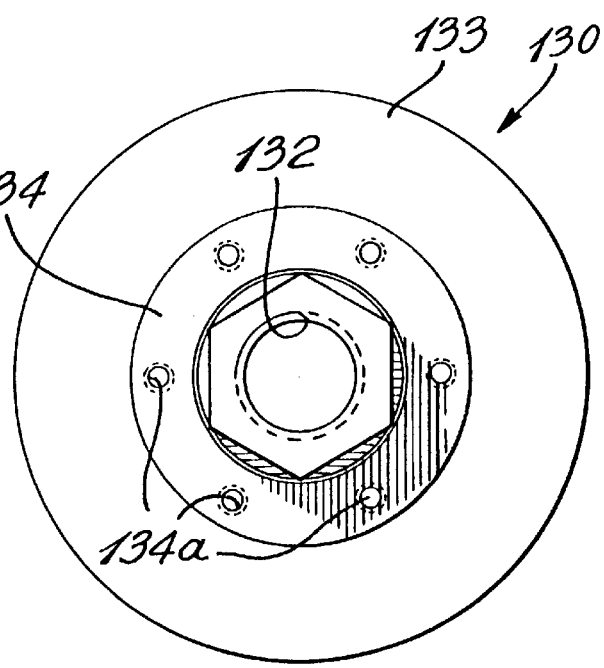

FIG. 10a and 10b illustrate an alternate type of extension attachment element 130. This modified version also has an outer threaded portion 131 and inner threaded surface portion 132; the surface portions are configured with the same purpose in mind as explained with respect to the threaded surface portions of attachment element 125. However, the attachment element 130 also includes a plurality of radial fins which are provided so as to facilitate the dissipation of heat into the ambient atmosphere from the device and any other elements in thermal communication with the device whether directly or indirectly (e.g. from fluid in the fluid pocket). A number of the radial fins are designated with the reference numeral 133. The attachment element 130 is also provided with means for attachment to a heat transfer plate member. In this respect the attachment element 130 is provided with an attachment flange 134; the attachment flange 134 is provided with screw threaded openings 134a for receiving screw or bolt means for fixing the attachment element 130 to a heat transfer plate member.

Figure 11:
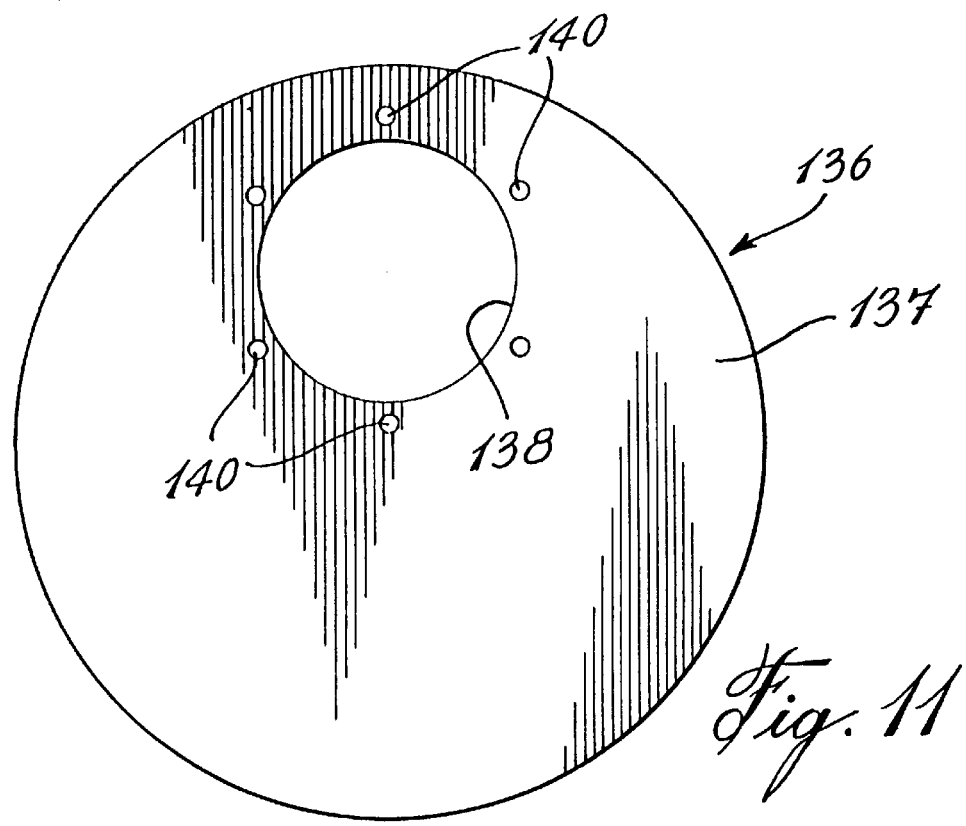
FIG. 11 is a front view of an example of a heat transfer plate member.

Turning to FIGS. 11 and 12, these figures relate to a heat transfer plate member 136. The plate member 136 has plate body 137 which is provided with an opening 138 around which is disposed a plurality of openings 140. The opening 140 are sized to receive the stem of a bolt or screw for fixing an extension attachment element to the plate member.

Referring to FIG. 12, this figure shows an attachment element 125 in the process of being attached to the heat transfer plate member 136; the attachment element 125 as shown in FIGS. 9a and 9b has a head element 141. As may be seen the head element 141 of the attachment element 125 is sized smaller than the opening 138 of the plate member 136 so that the head 141 may pass through the opening 138. On the other hand the flange 128 is sized larger than the opening 138 and its attachment openings 129 are sized and distributed so as to be able to line up with corresponding openings 140. As may be seen, the attachment element 125 is passed in the direction of the arrow 142 while the bolts 143 (only one bolt is shown) are passed in the direction of the arrow 144 for the attachment of the two elements together; the stem 145 of a bolt 142 is sized to pass through the opening 140 for engaging an opening 129 of the extension attachment element 125.

FIG. 13 shows an example monitoring apparatus in accordance with the present invention with the outer casing removed. As may be appreciated by referring to FIG. 13, an extension attachment element such as element 125 may as described above be screw attached to the heat transfer plate member 136. Once the extension element 125 is screw or bolt attached to the plate member 136, a detector element such as detector element 120 may in turn be screw attached to the inner threaded surface 127 of the extension element 125. In this case it is of course understood that the plate member 136, the extension element 125, and the relevant elements of the detector 120 are all of a thermally conductive material (e.g. a metal such as brass) so that heat may be transferred there between and any fluid in the fluid pocket as defined by elements mentioned above.

As may be seen from FIG. 13 the apparatus includes a platform 160 for seating various electrical components thereof. The platform may for example comprise a power supply means, an analogue to digital converter for treating the temperature signal from the temperature sensor 114, etc. The apparatus also has a housing 165 in which may be disposed a microprocessor for carrying out the function of the above mentioned controller element 22 and temperature reference generator 24 (see FIG. 1). The electrical components are of course suitably interconnected keeping in mind the purpose and function of the monitoring apparatus.

In accordance with the present invention the apparatus shown in FIG. 13 includes resistive heating elements 170 and a power cable for connection to a source of electrical power for energising these heating units. The electrical components of the apparatus also as mentioned include a suitable electronic circuit for monitoring the temperature of the wall element 107 of the detector 120 which defines at least a part of the fluid pocket component and for controlling the energisation of the heating units 170 as a function of such temperature e.g. in comparison with a changing reference temperature signal (i.e. so as to modulate the temperature of the wall element or component).

FIG. 14 shows the apparatus of FIG. 13 screw attached to a gate valve 180 which provides for access to the interior of a transformer; only a portion of the wall 181 of the transformer is shown. A power cable is designated with the reference numeral 185.

Figure 15:
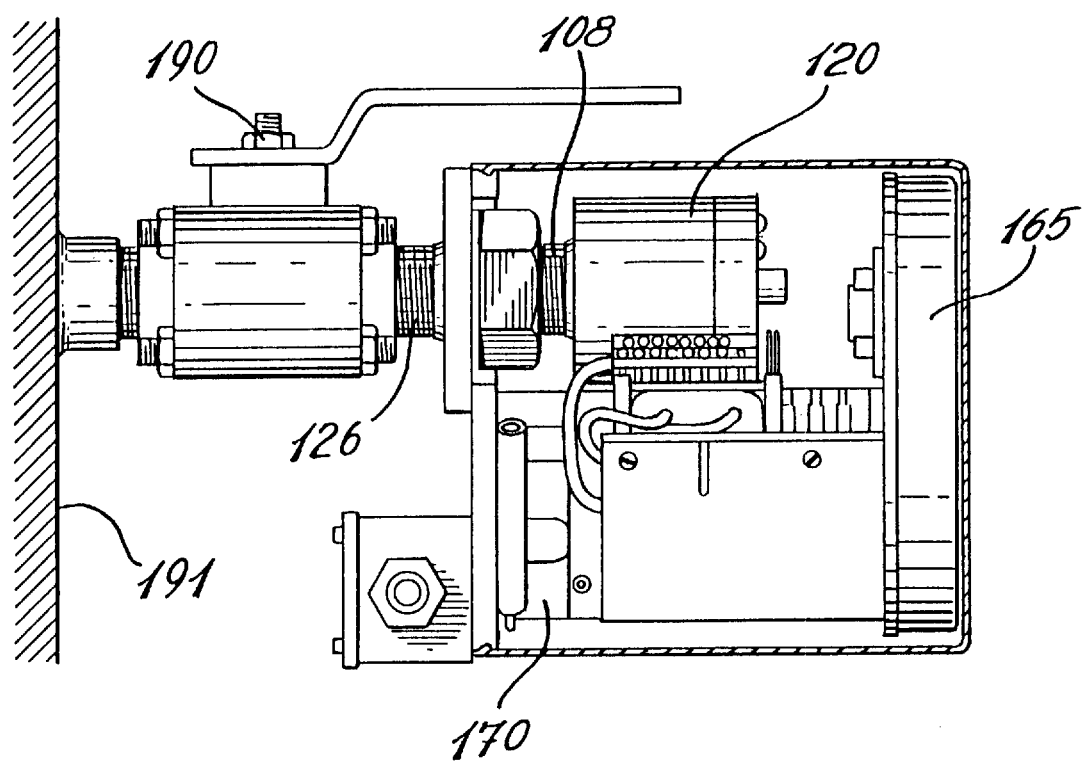
FIG. 15 is a schematic perspective view of an example monitoring apparatus in accordance with the present invention attached to a ball valve providing access to the interior of an electrical transformer, the main body of the transformer not being shown.

FIG. 15 shows the apparatus of FIG. 13 screw attached to a ball valve 190 which provides for access to the interior of a transformer; only a portion of the wall 191 of the transformer is shown.

It is of course understood that the valve may take on any other suitable form keeping in mind the intended use of the apparatus, i.e. to facilitate fluid flow by a thermal gradient.

Figure 16:
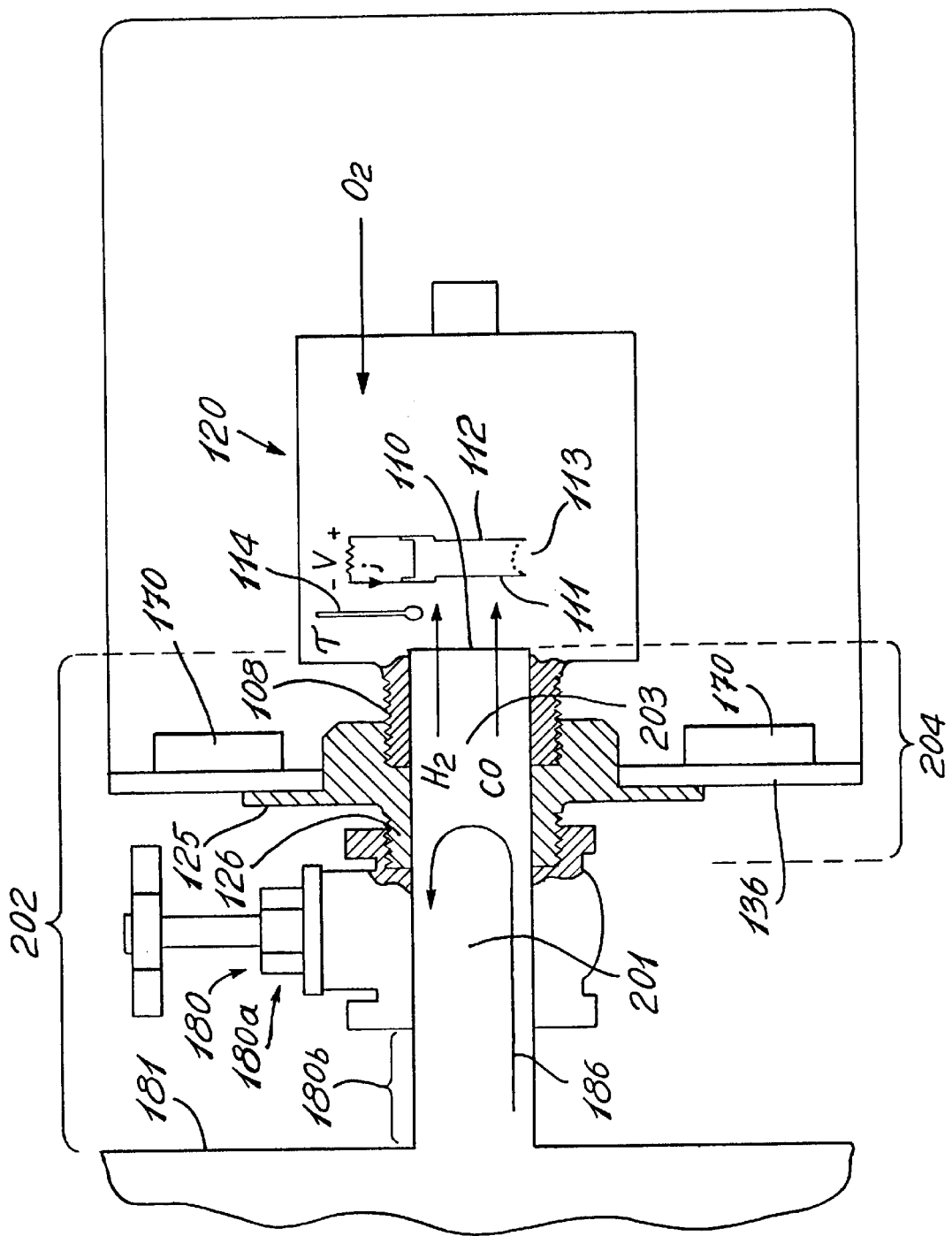
FIG. 16 is a schematic illustration of the combination as shown in FIG. 14.

FIG. 16 shows in schematic fashion the combination illustrated in FIG. 14. As may be appreciated, schematically, the combination illustrated in FIG. 16 is similar to that shown in FIG. 1 except for the presence of the detector 120 in place of the end cap 5; additionally for illustration purposes the controller and reference temperature signal generator block representations are not shown. The reference numerals in FIG. 16 are those used with respect to FIG. 7, 8a, 11, 12, 13 and 14, i.e. reference may be made to these figures for a more particular showing of the various parts of the combination. The fluid pocket is indicated generally by the reference numeral 201. The fluid pocket 201 has an overall length indicated by the reference numeral 202. The fluid pocket 201 comprises a fluid pocket component indicated generally by the reference numeral 203. The fluid pocket component 203 has an overall length indicated generally by the reference numeral 204. The fluid pocket 201 is defined by a housing which itself is defined by and comprises the detector 120, an extension attachment member 125 and a valve component 180 which includes valve element 180a and conduit element 180b. The detector 120 and the extension attachment element 125 together define a wall component which defines the fluid pocket component 203; the membrane 110 defines a part of the wall component defining the fluid pocket component. The arrow 186 shows fluid flow when the fluid in the fluid pocket is warmer than the fluid in the interior of the system. The temperature sensor 114 is connected to a suitable controller in a manner as described for the sensor 19 in FIG. 1. The controller controls the energisation of the heater elements 170 i.e. in a manner as described with respect to the controller 22 in FIG. 1. The comments with respect the modulation of the temperature of the wall component as given with respect to FIG. 1 apply to the operation of the apparatus in FIG. 16.

Figure 17:
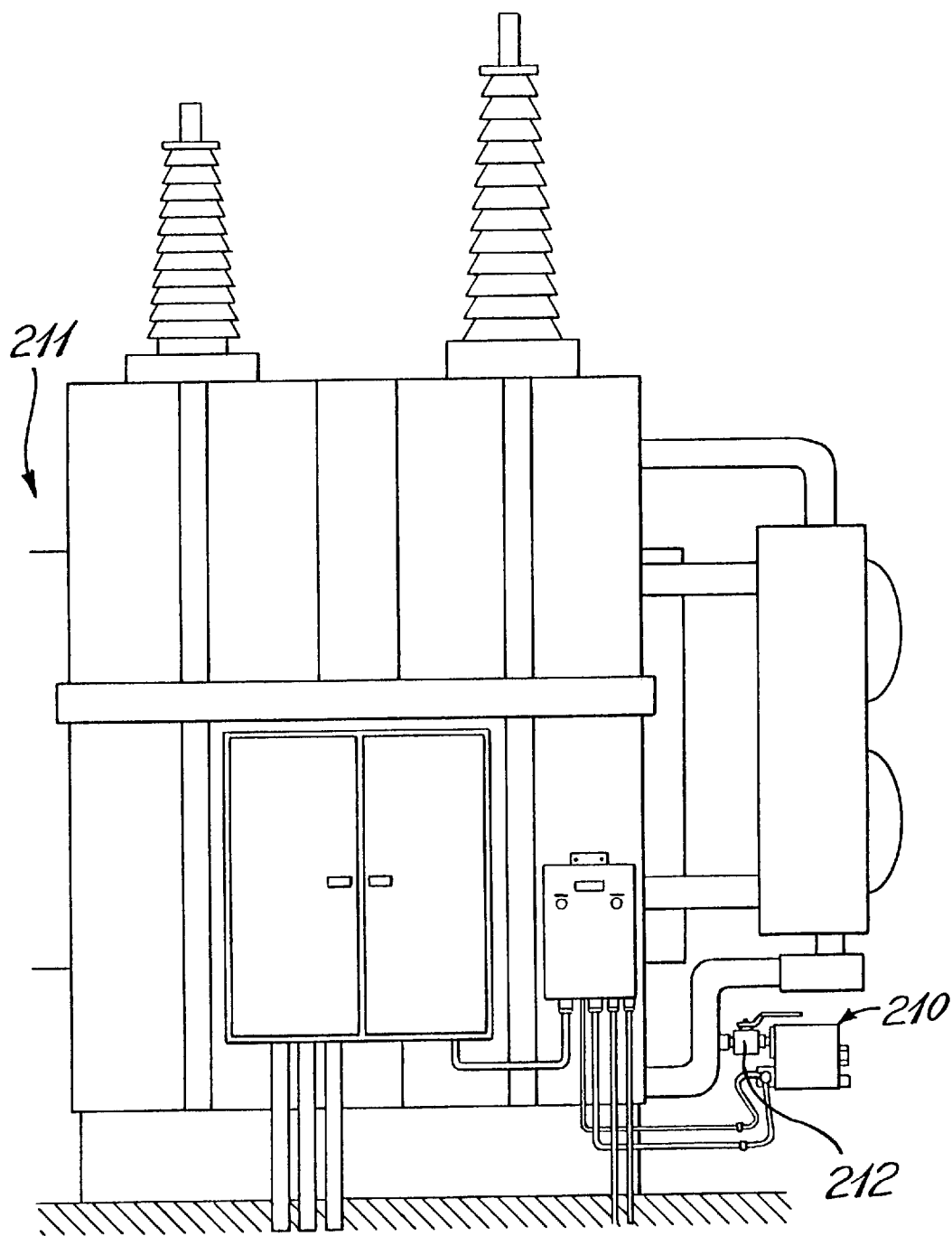
FIG. 17 is a schematic illustration of a monitoring apparatus of the present invention attached to an electrical transformer.

FIG. 17 shows a monitoring apparatus 210 of the present invention attached to a transformer 211 via valve 212, i.e. to a single opening in the return conduit leading from the cooling component back to the main body of the transformer. The apparatus could of course be attached at a different place.

Figure 18:
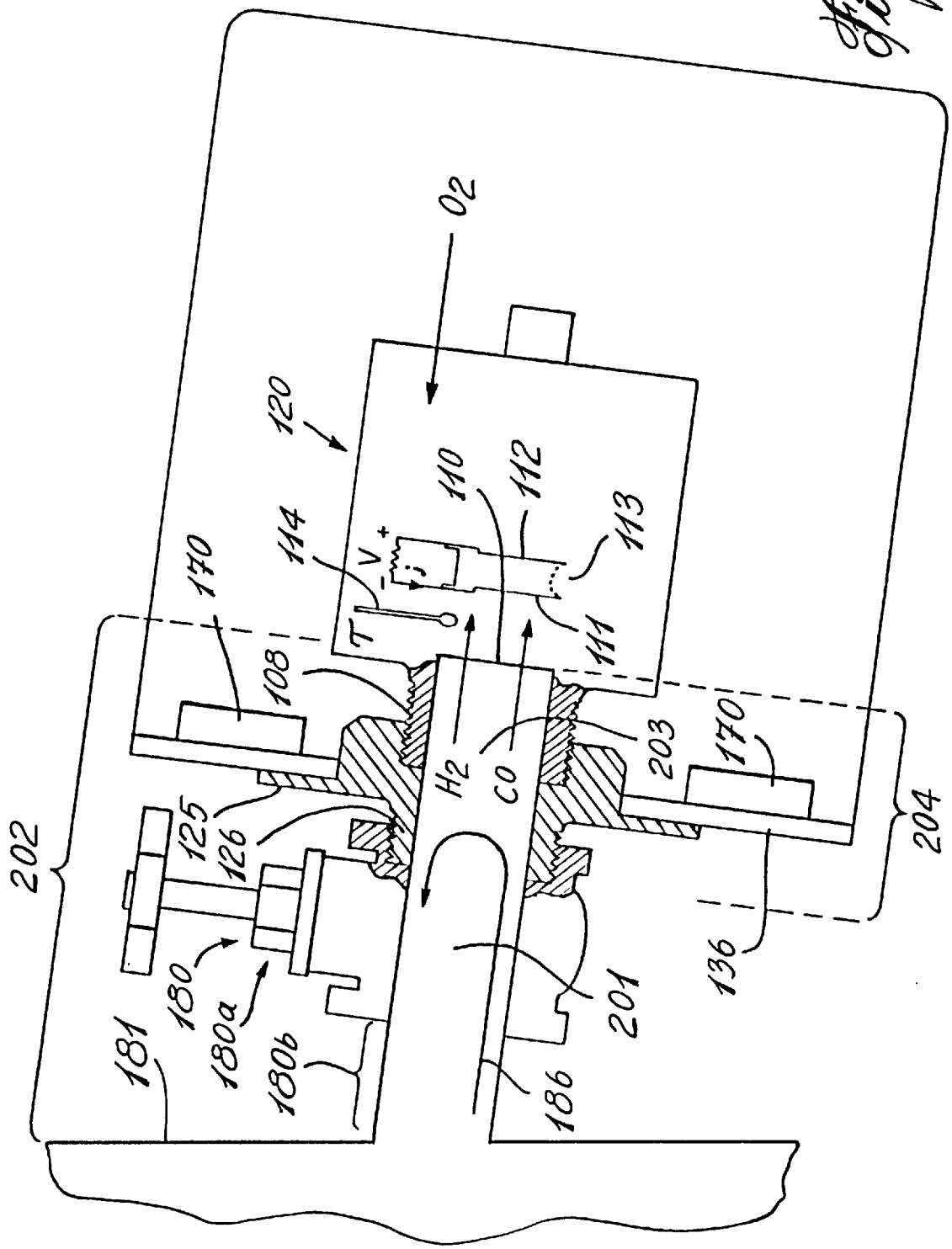
FIG. 18 is a schematic illustration of a modified version of the combination shown in FIG. 16.

FIG. 18 is a schematic illustration of a modified version of the combination shown in FIG. 16 wherein the fluid pocket is connected to the access opening by fluid conduit means, the fluid conduit means and the wall component define an essentially straight passageway inclined downwardly from the access opening; accordingly the same reference numerals are used in FIG. 18 to designate the same elements as in FIG. 16.

Although a monitoring apparatus has been described by way of example with an hydrogen gas detector, the apparatus of the present inventor may also be used with any other device for detecting other fault gases, moisture, and/or breakdown products.

The embodiments of the invention in which an exclusive property or privilege is claimed are as defined as follows:

1. In an apparatus for monitoring a substance in a dielectric fluid, said fluid being in an interior of an electrical system, the apparatus comprising:
   a) attachment means for attaching the apparatus to said electrical system so as to define a housing, said housing defining a fluid pocket, said fluid pocket being in fluid communication with a dielectric fluid access opening of the electrical system for fluid communication between the fluid pocket and said interior of the electrical system, and
   b) means for monitoring said substance in dielectric fluid in said fluid pocket,
the improvement wherein said apparatus comprises heat transfer means comprising a heat transfer element configured for thermal communication with dielectric fluid in said pocket, said heat transfer means comprising temperature modulation means for modulating the temperature of the heat transfer element between a first temperature and a second temperature.

2. An apparatus as defined in claim 1 wherein said heat transfer means comprises temperature modulation means for modulating the temperature of the heat transfer element between a first ambient temperature and a second temperature greater than said ambient temperature.

3. An apparatus as defined in claim 1 wherein the temperature difference between the first temperature and the second temperature is 20° C. or less.

4. An apparatus as defined in claim 1 wherein the temperature difference between the first temperature and the second temperature is 10° C. or less.

5. In an apparatus for monitoring a substance in a dielectric liquid, said liquid being in an interior of an electrical system, the apparatus comprising:
   a) a wall component defining a fluid pocket component, said wall component being configured for thermal communication with dielectric liquid in said pocket component,
   b) attachment means for attaching the apparatus to said electrical system so as to define a housing, said housing comprising said wall component and defining a fluid pocket, said fluid pocket being in fluid communication with a dielectric liquid access opening of the electrical system for liquid communication between the fluid pocket and said interior of the electrical system, said fluid pocket comprising said fluid pocket component, and
   c) means for monitoring said substance in dielectric liquid in said fluid pocket,
the improvement wherein said apparatus comprises heat transfer means, said heat transfer means comprising said wall component, said heat transfer means comprising temperature modulation means for modulating the temperature of the wall component between a first temperature and a second temperature.

6. An apparatus as defined in claim 5 wherein said heat transfer means comprises temperature modulation means for modulating the temperature of the wall element between a first ambient temperature and a second temperature greater than said ambient temperature.

7. An apparatus as defined in claim 5 wherein the temperature difference between the first temperature and the second temperature is 20° C. or less.

8. An apparatus as defined in claim 5 wherein the temperature difference between the first temperature and the second temperature is 10° C. or less.

9. An apparatus as defined in claim 5 wherein said means for monitoring comprises an isolation member for isolating the substance from the dielectric liquid, the member being disposed for contacting dielectric liquid in said fluid pocket component.

10. An apparatus as defined in claim 9 wherein said substance comprises a member of the group comprising a fault gas, moisture and a breakdown product.

11. An apparatus as defined in claim 9 wherein said isolation member comprises a membrane, permeable to said substance and impermeable to said dielectric liquid, said membrane being disposed for contacting, on one side thereof, dielectric liquid in said fluid pocket component.

12. An apparatus as defined in claim 11 wherein said substance comprises a fault gas.

13. An apparatus as defined in claim 5 wherein said means for monitoring comprises an isolation member for isolating the substance from the dielectric liquid, wherein said isolation member comprises a membrane, permeable to said substance and impermeable to said dielectric liquid, said membrane being disposed for contacting, on one side thereof, dielectric liquid in said fluid pocket component and wherein said substance comprises hydrogen gas.

14. An apparatus as defined in claim 13 wherein the temperature difference between the first temperature and the second temperature is 10° C. or less.

15. In a combination comprising
   an electrical system comprising a dielectric fluid in an interior thereof, said electrical system comprising a fluid access opening for fluid communication with said interior of the electrical system, and a monitoring component for monitoring a substance in the dielectric fluid, the monitoring component comprising:
  a) a housing, said housing defining a fluid pocket, said housing being attached to the electrical system such that the fluid pocket is in fluid communication with the fluid access opening for fluid communication between the fluid pocket and said interior of the electrical system, and
  b) means for monitoring said substance in dielectric fluid in said fluid pocket, the improvement wherein said monitoring component comprises heat transfer means comprising a heat transfer element configured for thermal communication with dielectric fluid in said fluid pocket, said heat transfer means comprising temperature modulation means for modulating the temperature of the heat transfer element between a first temperature and a second temperature.

16. A combination as defined in claim 15 wherein said heat transfer means comprises temperature modulation means for modulating the temperature of the heat transfer means between a first ambient temperature and a second temperature greater than said ambient temperature.

17. A combination as defined in claim 15 wherein the temperature difference between the first temperature and the second temperature is 20° C. or less.

18. A combination as defined in claim 15 wherein the temperature difference between the first temperature and the second temperature is 10° C. or less.

19. In a combination comprising
an electrical system comprising a dielectric liquid in an interior thereof, said electrical system comprising a liquid access opening for liquid communication with said interior of the electrical system, and
a monitoring component for monitoring a substance in the dielectric liquid, the monitoring component comprising:
  a) a housing, said housing comprising a wall component, said housing defining a fluid pocket, said housing being attached to the electrical system such that said fluid pocket is in liquid communication with said liquid access opening for liquid communication between the fluid pocket and said interior of the electrical system, said wall component defining a fluid pocket component, said fluid pocket comprising said fluid pocket component, said wall component being configured for thermal communication with dielectric liquid in said fluid pocket component, and
  b) means for monitoring said substance in dielectric liquid in said fluid pocket, the improvement wherein said monitoring component comprises heat transfer means, said heat transfer means comprising said wall component and temperature modulation means for modulating the temperature of the wall component between a first temperature and a second temperature.

20. A combination as defined in claim 19 wherein said fluid pocket is connected to said access opening by fluid conduit means, said fluid conduit means and said wall component defining an essentially straight horizontal passageway.

21. A combination as defined claim 19 wherein said fluid pocket is connected to said access opening by fluid conduit means, said fluid conduit means and said wall component defining an essentially straight passageway inclined downwardly from the access opening.

22. A combination as defined in claim 20 wherein said passageway has a minimum diameter d and a length l wherein the ratio of l to d is 6 to 1 or less.

23. A combination as defined in claim 20 wherein said detection means comprises an isolation member for isolating the substance from the dielectric liquid, the member being disposed for contacting dielectric liquid in said fluid pocket component.

24. An apparatus as defined in claim 22 wherein said substance comprises a member of the group comprising a fault gas, moisture and a breakdown product.

25. An apparatus as defined in claim 20 wherein said isolation member comprises a membrane, permeable to said substance and impermeable to said dielectric liquid, said membrane being disposed for contacting, on one side thereof dielectric liquid in said fluid pocket component.

26. An apparatus as defined in claim 25 wherein said substance comprises a fault gas.

27. A combination as defined in claim 23 wherein said passageway has a minimum diameter d and a length l wherein the ratio of l to d is 6 to 1 or less.

28. A combination as defined in claim 27 wherein the temperature difference between the first temperature and the second temperature is 10° C. or less.

29. A combination as defined in claim 26 wherein said passageway has a minimum diameter d and a length l wherein the ratio of l to d is 6 to 1 or less.

30. A combination as defined in claim 29 wherein the temperature difference between the first temperature and the second temperature is 10° C. or less.

31. An apparatus for inducing circulation of a fluid, in an interior of a system, between said interior and a fluid pocket, the apparatus comprising:
  a) attachment means for attaching the apparatus to said system so as to define a housing, said housing defining a fluid pocket, said fluid pocket being in fluid communication with a fluid access opening of the system for fluid communication between the fluid pocket and said interior of the system, and
  b) heat transfer means comprising a heat transfer element configured for thermal communication with fluid in said pocket, said heat transfer means comprising temperature modulation means for modulating the temperature of the heat transfer element between a first temperature and a second temperature.

32. An apparatus as defined in claim 31 wherein said system is an electrical system and said fluid is a dielectric fluid.

33. An apparatus as defined in claim 31 wherein said heat transfer means comprises temperature modulation means for modulating the temperature of the heat transfer element between a first ambient temperature and a second temperature greater than said ambient temperature.

34. An apparatus as defined in claim 31 wherein the temperature difference between the first temperature and the second temperature is 10° C. or less.

35. A method for inducing circulation of a fluid, in an interior of a system, between said interior and a fluid pocket, said fluid pocket being in fluid communication with a fluid access opening of the system for fluid communication between the fluid pocket and the interior of the system, said method comprising modulating the temperature of a heat transfer element in thermal communication with fluid in said pocket, between a first temperature and a second temperature.

36. A method as defined in claim 35 wherein said system is an electrical system and said fluid is a dielectric fluid.

37. A method as defined in claim 35 comprising modulating the temperature of the heat transfer element between a first ambient temperature and a second temperature greater than said ambient temperature.

38. A method as defined in claim 35 wherein the temperature difference between the first temperature and the second temperature is 20° C. or less.

39. A combination comprising a system comprising a fluid in an interior thereof, said system comprising a fluid access opening for fluid communication with said interior of the system, and a component for inducing circulation of the fluid between said interior and a fluid pocket, said component comprising:

a) a housing, said housing defining a fluid pocket, said housing being attached to the said system such that the fluid pocket is in fluid communication with the fluid access opening for fluid communication between the fluid pocket and said interior of the system, and b) heat transfer means comprising a heat transfer element configured for thermal communication with fluid in said fluid pocket, said heat transfer means comprising temperature modulation means for modulating the temperature of the heat transfer element between a first temperature and a second temperature.

40. An apparatus as defined in claim 39 wherein said system is an electrical system and said fluid is a dielectric fluid.

41. A combination as defined in claim 39 wherein said heat transfer means comprises temperature modulation means for modulating the temperature of the heat transfer element between a first ambient temperature and a second temperature greater than said ambient temperature.

42. A combination as defined in claim 39 wherein the temperature difference between the first temperature and the second temperature is 10° C. or less.

* * * * *